United States Patent [19]

Silverman et al.

[11] 3,957,882
[45] May 18, 1976

[54] 2-HALOETHYLSULFONYL PHOTOGRAPHIC HARDENER COMPOUNDS, COMPOSITIONS, ARTICLES AND PREPARATION PROCESSES

[75] Inventors: Robert A. Silverman; Charles J. Wright, both of Rochester, N.Y.

[73] Assignee: Eastman Kodak Company, Rochester, N.Y.

[22] Filed: May 2, 1974

[21] Appl. No.: 466,092

Related U.S. Application Data

[62] Division of Ser. No. 293,697, Sept. 29, 1972, Pat. No. 3,839,042.

[52] U.S. Cl............................ 260/607 A; 260/607 R
[51] Int. Cl.²................ C07C 147/02; C07C 147/06
[58] Field of Search.... 260/607 A, 607 AL, 607 AR

[56] References Cited
UNITED STATES PATENTS

| | | | |
|---|---|---|---|
| 2,802,035 | 8/1957 | Fincke | 260/607 A |
| 3,136,687 | 6/1964 | Hensley et al. | 260/607 A |

OTHER PUBLICATIONS
Org. Chem. of Sulfur by Chester M. Suter pp. 735–738.
J. A. Chem. Soc. Vol. 69 p. 1176 (1947).
J. Biochem. Vol. 40 pp. 743–745 (1946).

*Primary Examiner*—Lewis Gotts
*Assistant Examiner*—D. R. Phillips
*Attorney, Agent, or Firm*—J. J. Ruch

[57] ABSTRACT

Photographic elements are disclosed containing a hydrophilic colloid layer hardened with a compound having the structural formula:

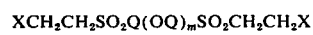

wherein X in each occurrence is halogen, Q is an aliphatic or phenyl substituted aliphatic divalent hydrocarbon radical having from 1 to 6 aliphatic carbon atoms and *m* is an integer of from 0 to 3 inclusive. The hardener also serves as an anti-foggant in photographic applications. Preferred are novel hardening and anti-fogging compounds having the structural formula:

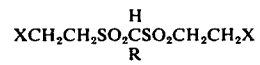

in which X is halogen and R is hydrogen, phenyl or alkyl having from 1 to 6 carbon atoms.

5 Claims, No Drawings

# 2-HALOETHYLSULFONYL PHOTOGRAPHIC HARDENER COMPOUNDS, COMPOSITIONS, ARTICLES AND PREPARATION PROCESSES

This is a division of application Ser. No. 293,697, filed Sept. 29, 1972, now U.S. Pat. No. 3,839,042, issued Oct. 1, 1974.

This invention relates to hardeners containing plural 2-haloethylsulfonyl radicals. In one aspect this invention relates to certain novel bis(2-haloethyl)sulfonyl compounds. In another aspect this application relates to hardenable hydrophilic colloid compositions containing bis(2-haloethyl)sulfonyl hardeners, which in photographic applications also exhibit anti-fogging characteristics, and to photographic elements incorporating such compositions. In a further aspect this invention relates to processes for preparing such compositions and photographic elements.

In the photographic arts hydrophilic colloids---typically refined gelatins--have been used to suspend silver halide grains and thereby to form radiation-sensitive compositions which when coated onto suitable supports are capable of forming photographic elements. Typically a variety of addenda are employed to alter the properties of both the gelatin and the silver halide grains. It has been recognized previously in the art that without special modifiers hydrophilic colloids such as gelatins ingest large quantities of water when brought into contact with aqueous solutions, causing appreciable swelling, and are easily abraded. Also, unmodified gelatin coatings tend to melt at relatively low temperatures, thereby limiting their temperature range of utility. To alter these deficiencies of unmodified photographic gelatins it has heretofore been recognized that certain addenda generically designated as "hardener addenda" or simply "hardeners" may be incorporated into radiation-sensitive compositions and coatings to obviate at least one of the above undesirable gelatin characteristics.

In order to serve the needs of the photographic arts it is desirable not only that a hardener ameliorate the deficiencies of gelatins as noted above, but that the hardener meet certain additional practical criteria. For example, the hardener should cause hardening or setting of the emulsion sufficiently slowly to permit coating of the photographic emulsion onto a support, but it should not set up so slowly that after-hardening takes place--i.e. the emulsion continues to harden undesirably during storage of a fabricated photographic element. Also, the hardener should possess sufficiently low levels of toxicity so as not to pose a significant hazard to manufacturing personnel. Further, the hardener should not undesirably reduce or interfere with the desired photographic properties of the element into which it is incorporated. For example, the hardener should not contribute to the reduction of silver halide to produce fogging of a photographic emulsion or coating. These criteria for hardeners are all the more challenging when it is borne in mind that the composition of photographic gelatins are themselves not fully understood and that the mechanisms of hardening are not entirely appreciated.

In addition to the above considerations, it must be recognized that the hardener is only a part of what typically is a comparatively complex photographic system. For example, in addition to the radiation-sensitive silver halide and the gelatin to be hardened photographic emulsions typically contain numerous additional addenda. With so many criteria being applied to hardeners and in view of the complexity of photographic emulsions it is not then surprising that there is presently no known way of predicting the suitability of significantly differing types of compounds as hardeners in photographic emulsions, and the art has relied upon empirical methods to discover new types of hardeners. Beyond this, the selection of hardeners having both satisfactory hardening and other desirable and advantageous photographic characteristics permitting their substitution for or supplementing of other photographic addenda has remained in the realm of chance discovery.

A number of bis(2-haloethyl) compounds are known. Bis(2-chloroethyl) sulfide, mustard gas, is best known for its toxicity. The preparation of 2,2-bis(2-chloroethylsulfonyl) propane is disclosed by Buchi et al Helv. Chim. Acta. 42, 1368 (1959). Tesoro U.S. Pat. No. 3,201,434, issued Aug. 17, 1965, teaches the utility of certain bis(2-chloroethyl) compounds containing hydrocarbon and ether linking radicals (but excluding methylene linking radicals) as crosslinking agents for fibrous polymers. Tesoro, however, does not teach or suggest any utility of these crosslinking agents with hydrophilic colloids nor utility in a photographic environment. Belgium Pat. No. 606,234, issued July 18, 1961, teaches the use of bis(2-chloroethyl) sulfone as a protein hardener; however, its toxicity is comparable to that of mustard gas. Additionally, bis(2-chloroethyl) sulfone possesses comparatively inferior hardening characteristics at elevated temperatures and with respect to after-hardening characteristics. Burness Pat. No. 3,106,468, issued Oct. 8, 1963, teaches the use of bis(2-haloethyl) urea type compounds as photographic gelatin hardeners. None of the above patents teach or suggest the utility of bis(2-haloethylsulfonyl) compounds as anti-foggants in photographic compositions and elements.

It is one object of this invention to provide a new class of compounds having a combination of desirable characteristics rendering them useful as hardeners for hydrophilic colloids.

It is a second object of this invention to provide a new class of compounds capable of functioning simultaneously as hardener and anti-foggant addenda in radiation-sensitive hydrophilic colloids--i.e. photographic emulsions. It is another object to provide novel hydrophilic colloid compositions utilizing a hardener that is free of objectionable physiological activity, that is capable of producing hardening at ambient and elevated temperatures and that exhibits a desirable rate of hardening.

It is a more specific object to provide novel photographic compositions and elements containing a photographic emulsion that is hardened both at ambient and elevated temperatures, that is free of objectionable physiological activity and that exhibits anti-foggant characteristics.

It is an additional object to provide a process of hardening a hydrophilic colloid.

In a broad aspect this invention contemplates adding to a hydrophilic colloid a hardening concentration of a compound having two 2-haloethylsulfonyl radicals coupled through an aliphatic or phenyl substituted aliphatic divalent linking radical to form a novel hardened hydrophilic colloid composition. The preferred hardeners are a novel class of compounds having two 2-haloethylsulfonyl radicals coupled through an unsubstituted or hydrocarbon-substituted methylene linking radical.

It has been discovered quite unexpectedly that the 2-haloethylsulfonyl compounds defined as useful in the practice of this invention produce in hydrophilic colloids a combination of useful hardening characteristics and when utilized in radiation-sensitive colloids--e.g. photographic emulsions, produce both the desired combination of hardening characteristics and anti-fogging characteristics. These 2-haloethylsulfonyl compounds harden hydrophilic colloids to reduce swelling and abrasion thereof. Additionally, these 2-haloethylsulfonyl compounds harden hydrophilic colloids at elevated temperatures. Still further, the colloids hardened with these 2-haloethylsulfonyl compounds are not hardened so rapidly as to interfere with their being coated onto a support, yet they are free of undesirable afterhardening characteristics. At the same time colloids hardened with the 2-haloethylsulfonyl compounds utilized in the practice of this invention do not pose a hazard to manufacturing personnel. It is quite surprising that hydrophilic colloids hardened with 2-haloethylsulfonyl compounds according to this invention possess this combination of hardening, high temperature hardening and low physiological activity characteristics. It is even more surprising that, when the hydrophilic colloid is a radiation-sensitive colloid, such as a photographic emulsion, the 2-haloethylsulfonyl compounds of this invention perform both the functions of hardening and high-temperature hardening and additionally are capable of functioning as anti-foggant addenda.

A class of compounds which can be combined with hydrophilic colloids according to this invention to provide a combination of desirable colloid hardening characteristics and, in photographic applications, antifogging properties are defined by the structural formula:

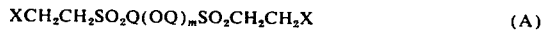

XCH₂CH₂SO₂Q(OQ)ₘSO₂CH₂CH₂X    (A)

wherein X is halogen, Q is an aliphatic or phenyl substituted aliphatic divalent hydrocarbon radical having from 1 to 6 aliphatic carbon atoms and *m* is an integer of from 0 to 3 inclusive.

Preferred compounds as of the type set forth above are those novel compounds which can be defined by the structural formula:

$$\underset{R}{\overset{H}{\text{XCH}_2\text{CH}_2\text{SO}_2\text{C}\text{SO}_2\text{CH}_2\text{CH}_2\text{X}}}$$   (B)

in which X is halogen and R is hydrogen, phenyl or alkyl having from 1 to 6 carbon atoms. Specific preferred novel compounds useful in accordance with this invention include bis(2-haloethylsulfonyl)methane; 1,1-bis(2-haloethylsulfonyl)-ethane; 1,1-bis(2-haloethylsulfonyl)propane; 1,1-bis(2-haloethylsulfonyl)butane; 1,1-bis(2-haloethylsulfonyl)-pentane; 1,1-bis(2-haloethylsulfonyl)hexane; 1,1-bis(2-haloethylsulfonyl)heptane; and alpha, alpha-bis(2-haloethyl-sulfonyl)toluene. The haloethyl radical can be chloroethyl, bromoethyl and the like.

These novel compounds can be prepared by reacting the aldehyde or acetal corresponding to the divalent methylene linking radical desired with 2-haloethanethiol. This produces the bis(2-haloethylsulfide) compound corresponding to the desired compound. The sulfide can then be converted to the bis(2-haloethylsulfonyl) methane compound desired using an oxidizing agent such as hydrogen peroxide, m-chloroperbenzoic acid, and the like.

It is additionally recognized that compounds within the purview of formula (A) above may be utilized in the practice of this invention in addition to those preferred compounds set forth by formula (B). Generally the two 2-haloethylsulfonyl radicals may be joined by any aliphatic or phenyl substituted aliphatic divalent hydrocarbon or ether linking radical. Alkylene, alkenylene, oxaalkylene and dioxaalkylene divalent linking radicals are specifically contemplated.

Such compounds include bis(2-haloethylsulfonyl) alkanes, bis(2-haloethylsulfonyl) alkenes and bis(2-haloethylsulfonyl) oxaalkanes, such as dialkyl ethers and dioxaalkanes. Exemplary of these are 1,2-bis(2-haloethylsulfonyl)ethane; 1,3-bis(2-haloethylsulfonyl)-propane; 1,4-bis(2-haloethylsulfonyl)butane; 1,4-bis(2-haloethylsulfonyl)-2-butene; 1,5-bis(2-haloethylsulfonyl)-2-pentene; 1,6-bis(2-haloethylsulfonyl)-2-hexene and 1,6-bis(2-haloethylsulfonyl)-3-hexene; 1,5-bis(2-haloethylsulfonyl)pentane; bis(2-haloethylsulfonylmethyl) ether; bis[2-(2-haloethylsulfonyl)ethyl] ether; bis[4-(2-halosulfonyl)butyl] ether; 1,6-bis(2-haloethylsulfonyl)-2,5-dioxahexane and 1,8-bis(2-haloethylsulfonyl)3,6-dioxaoctane. The haloethyl moiety may be chloroethyl, bromoethyl and the like. The processes for preparing these known compounds are, of course, known in the art and form no part of this invention. For example, the Tesoro patent noted above teaches the preparation of compounds of this general type. Other preparations are reported in the Journal of Organic Chemistry, vol. 12, at pp. 249 and 255. For ease of synthesis it is preferred that Q in each occurrence in formula (A) be identically chosen.

The hydrophilic colloids which are hardenable by the above bis(2-haloethylsulfonyl) compounds can be formed from one or more hydrophilic, water permeable colloid forming natural or synthetic polymers. Specific polymers which can be hardened according to the practice of this invention include hardenable polymers such as gelatin, colloidal albumin, acid or water-soluble vinyl polymers, cellulose derivatives, proteins, various polyacrylamides, dispersed polymerized vinyl compounds, particularly those which increase the dimensional stability of photographic materials as exemplified by amine-containing polymers of alkyl acrylates, methacrylates, acrylic acid, sulfoalkyl acrylates and methacrylates, acrylic acid-acrylate copolymers, and the like. Suitable synthetic polymers include those described, for example, in Nottorf U.S. Pat. No. 3,142,568, issued July 28, 1964; White U.S. Pat. No. 3,193,386, issued July 6, 1965; Houck et al. U.S. Pat. No. 3,062,674, issued Nov. 6, 1962; Houck et al. U.S. Pat. No. 3,220,844, issued Nov. 30, 1965; Ream et al. U.S. Pat. No. 3,287,289, issued Nov. 22, 1966; Dykstra U.S. Pat. No. 3,411,911, issued Nov. 19, 1968; Smith U.S. Pat. No. 3,488,708 issued Jan. 6, 1970, and Dykstra Canadian Pat. No. 774,054. The use of the hardeners of this invention with polymers having active ketomethylene groups, as described in Smith U.S. Pat. No. 3,488,708, cited above, is the separate invention of Osterhoudt and Smith disclosed in concurrently filed patent application U.S. Ser. No. 293,695, filed Sept. 29, 1972, now abandoned, titled "Photographic Element Comprising a Vinylsulfonyl Crosslinked Polymer Having Active Ketomethylene Groups".

The hydrophilic colloid to be hardened is typically utilized as a layer or coating on a support. A wide variety of supports, such as polymeric film, wood, metal, glass and the like, may be utilized to form hydrophilic colloid coated elements according to this invention. Where a photographic element is contemplated the support can take such forms as those set forth in paragraph X of Product Licensing Index, Vol. 92, December 1971, publication 9232, at page 108.

Where the hydrophilic colloid is to be utilized in combination with a support to form a photographic element, it will contain in or on it a radiation-sensitive material. This material can be panchromatic or orthochromatic material, sensitive only to X-rays or sensitive to selected portions of the electromagnetic spectrum. In one form of the invention the radiation-sensitive portion of the photographic element can contain a single, unitary hydrophilic colloid layer having dispersed therein the radiation-sensitive material together with photographic addenda to form a photographic emulsion layer or coating. In alternative forms the radiation-sensitive portion of the photographic element can comprise a plurality of layers with the radiation-sensitive material or materials being contained in some or all of the layers. For example, as is characteristic of color photography, a plurality of layers can be present sensitized within separate segments of the visible spectrum.

Suitable radiation-sensitive colloids which can be employed in practicing this invention are sensitive to electromagnetic radiation and include such diverse materials as silver salts, zinc oxide, photosensitive polycarbonate resins and the like. Silver halides are preferred radiation-sensitive materials and are preferably associated with a colloid dispersion vehicle to form an emulsion coating or layer. Specific preferred silver halide containing photographic emulsions and processes for their preparation and use are disclosed in paragraph I of Product Licensing Index, Vol. 92, December 1971, publication 9232, at page 107. The radiation-sensitive colloids can additionally include a variety of conventional photographic addenda, such as development modifiers, plasticizers and lubricants, brighteners, spectral sensitization agents and color forming materials as set forth in paragraphs IV, XI, XIV, XV and XXII, respectively, of Product Licensing Index, Vol. 92, December 1971, publication 9232, at pages 107–110. While it is contemplated that the 2-haloethylsulfonyl compounds utilized in the practice of this invention may serve as the sole hardener and/or anti-foggant addenda present, it is appreciated that other conventional hardeners and/or anti-foggants may also be incorporated into the hydrophilic colloid, such as those set forth, for example, in paragraphs V and VII of Product Licensing Index, Vol. 92, December 1971, publication 9232, pages 107 and 108.

While a wide range in concentrations of 2-haloethylsulfonyl compounds disclosed herein is effective for achieving the desired combination of hardening characteristics in hydrophilic colloids and, in radiation-sensitive colloids, anti-foggant characteristics, a particularly effective concentration is from about 0.5 to 6 percent by weight, based on the weight of the hardenable material present in the hydrophilic colloid--i.e. the dry weight (excluding the weight of any water present) of the gelatin or the like making up the colloid. It has been found that about 1 percent to about 3 percent by weight, based on the weight of the hardenable material present in the hydrophilic colloid, is particularly effective in achieving both superior hardening and, in radiation-sensitive colloids, anti-fogging activity.

In order to achieve uniform hardening and/or anti-fogging activity it is preferred to uniformly disperse the 2-haloethylsulfonyl compounds in the hydrophilic colloid to be modified. According to one technique, referred to as forehardening, the 2-haloethylsulfonyl compound is dissolved in a volatile solvent, such as a lower alkyl alcohol, acetone, etc., and the solution is uniformly blended with the hydrophilic colloid to be modified. Typically the hydrophilic colloid has at this stage an amount of water associated therewith which is in excess of that ultimately desired. Immediately after blending the colloid is deposited on a suitable support to form a layer or coating. The colloid is then hardened on the support and such volatile solvent and/or dispersants as are associated with the colloid and 2-haloethylsulfonyl compound solution are removed by evaporation either at ambient or elevated temperatures, typically below about 100°C.

It is also contemplated that the 2-haloethylsulfonyl compounds of this invention may be associated with hydrophilic colloids after they have been positioned on supports as coatings or layers. The support bearing a hydrophilic colloid coating to be hardened may be immersed in a solution containing the 2-haloethylsulfonyl compound therein so that the solution either surface hardens the colloid layer or permeates and uniformly hardens the colloid layer. This hardening technique, referred to as prehardening, finds particular utility in hardening certain photographic elements after exposure but before processing to form the photographic image. In this way a level of hardening can be imparted to the photographic element that might be objectionable in storage and use prior to exposure, but which is quite advantageous in preventing damage to the colloid layer of the photographic element during processing.

To further illustrate this invention the following specific, exemplary embodiments are set forth:

Preparation of Hardeners:

| | |
|---|---|
| Hardener I | Bis(2-chloroethylsulfonylmethyl) Ether |
| Hardener II | Bis[2-(2-chloroethylsulfonyl)ethyl] Ether |
| Hardener III | Bis[4-(2-chloroethylsulfonyl)butyl] Ether |
| Hardener IV | 1,8-Bis(2-chloroethylsulfonyl)-3,6-dioxaoctane |
| Hardener V | 1,2-Bis(2-chloroethylsulfonyl)ethane |
| Hardener VI | 1,3-Bis(2-chloroethylsulfonyl)propane |
| Hardener VII | 1,4-Bis(2-chloroethylsulfonyl)butane |
| Hardener VIII | 1,5-Bis(2-chloroethylsulfonyl)pentane |
| Hardener IX | trans-1,4-Bis(2-chloroethylsulfonyl)-2-butene |

Although not recognized to be hardeners, the foregoing compounds are per se known to the art as well as procedures for their preparation. To prepare Hardener I 5-oxa-3,7-dithianonane-1,9-diol is prepared by the reaction of two molar proportions of sodium 2-hydroxyethyl mercaptide with bis(chloromethyl) ether in methanol followed by evaporation of the solvent. The bis sulfide is then oxidized to the disulfone in hydrogen peroxide according to the procedure of Schultz et al J. Org. Chem. 28, 1140 (1963). The resulting disulfone diol is converted to its dichloride, by refluxing a solution of 22 g of the diol and 0.6 g of N,N-dimethylformamide in 240 ml of acetonitrile and treating at reflux with 23 grams thionyl chloride. After a 3-hour reflux period the solution is treated with charcoal, filtered and evaporated on a 40°C bath. Recrystallization from methanol gives a colorless chloride in rather a high yield and has a m.p. of 83°–84°C.

Hardeners II, III and IV can be prepared in the same general manner starting with bis(2-chloroethyl) ether, bis(4-chlorobutyl) ether and 1,8-dichloro-3,6-dioxaoctane, respectively. Hardener V can be prepared by the procedure of Price and Roberts, J. Org. Chem., 12, 255 (1947). Hardeners VI, VII and VIII can be prepared by the procedure of Schultz et al, J. Org. Chem., 28, 1140 (1963). Hardener IX can be prepared in the same general manner as Hardener I starting with trans-1,4-dichloro-2-butene.

In addition to the foregoing hardeners additional representative hardeners are prepared which are novel compounds falling within structural formula B set forth previously.

Hardener X Bis(2-chloroethylsulfonyl)methane

This compound is prepared from the sulfide (E. J. Gasson et al J. Chem. Soc. 1948, 45) by oxidation with hydrogen peroxide according to H. S. Schultz et al J. Org. Chem. 28, 1140 (1963). The sulfonediol obtained is a colorless solid, having a m.p. of 71.5 to 77°C. A solution of 22 g of the diol and 0.6 g of N,N-dimethylformamide in 240 ml of acetonitrile is treated at reflux with 23 g of thionyl chloride. After a 3-hour reflux period the solution is treated with charcoal, filtered and evaporated on a 40°C bath. The resulting semi-solic residue is first crystallized from n-propanol and then from 3:1 toluene-ligroin to give 7.5 g of colorless solid having a m.p. of 108°–109.5°C. Upon analysis the following is found for

| $C_5H_{10}Cl_2O_4S_2$: | Calculated | C, 22.3; H. 3.8; S, 23.8 |
|---|---|---|
| | Found | C, 22.3; H, 3.5; S, 23.6 |

Hardener XI 1,1-Bis(2-chloroethylsulfonyl) ethane a. 1,1-Bis(2-chloroethylthioethane) is first prepared by heating to reflux, a solution of 16.2 g of acetal and 26.4 g of 2-chloroethanethiol and 0.05 g of p-toluenesulfonic acid in 75 ml of benzene. The benzene-ethanol azeotrope is distilled slowly through a short packed column until reaction appears complete. This solution is cooled, filtered, neutralized with aqueous sodium bicarbonate and then evaporated to give 28.8 g of colorless oil. The nmr spectrum appears reasonable in confirming the product.

b. To a solution of 13.1 g of the above sulfide in 450 ml of dry chloroform is gradually added with stirring, 50.3 g of 85 percent m-chloroperbenzoic acid at 25° to 27°C. After being heated at 35° to 40°C for 3.5 hours the mixture is cooled below 0°C and filtered. The filtrate is then shaken with several portions of cold, aqueous sodium bicarbonate solution until the aqueous extract no longer gives a precipitate when acidified. The chloroform solution is dried over magnesium sulfate and evaporated. Recrystallization from ethanol produces 13 g of colorless solid having a m.p. of 85° to 89°C.

Upon analysis the following is obtained for

| $C_6H_{12}Cl_2O_4S_2$ | Calculated | C, 25.4; H, 4.2; Cl, 25.1 |
|---|---|---|
| | Found | C, 25.7; H, 4.2; Cl, 24.8 |

Hardener XII α,α-Bis(2-chloroethylsulfonyl)toluene a. First formed is α,α-Bis(2-chloroethylthio)toluene from a solution of 10.5 g of benzaldehyde and 19.2 g of 2-chloroethanethiol in ether saturated with hydrogen chloride at a reaction temperature of −10° to −15°C. After 18 hours at 6°C, the ether is evaporated, replaced with benzene, and the resulting product isolated as described above. The nmr spectrum conforms to the expected structure.

b. α,α-Bis(2-chloroethylsulfonyl)toluene is prepared by the oxidation of the sulfide with m-chloroperbenzoic acid as in Example XIV but with the reaction temperature held at 25° to 30°C for 4.5 hours after the addition. After filtration of the cold (−5°C) reaction mixture, the chloroform solution is evaporated on a 40°C bath to dryness. Recrystallization from benzene and then methanol yields colorless crystals having a m.p. 106° to 108°C in 83 percent yield.

Upon analysis the following is found for

| $C_{11}H_{14}Cl_2O_4S_2$ | Calculated | C, 38.2; H, 4.1; Cl, 20.5 |
|---|---|---|
| | Found | C, 38.4; H, 4.5; Cl, 20.8 |

It is recognized that bis(2-bromoethylsulfonyl) hardeners can be prepared according to the illustrative procedures set forth above.

Colloid Hardening and Anti-Fogging

To illustrate the hardening and anti-fogging characteristics of Hardeners I through XII, which are considered to be representative of this invention, these hardeners are added in amounts expressed as percent by weight, based on the gelatin weight, to portions of high speed gelatin silver bromoiodide photographic emulsion with one portion of the emulsion being maintained hardener-free and identified as a control. The hardener is diluted in a solvent, such as acetone or methanol, and blended with photographic emulsion. Each emulsion is immediately thereafter coated onto a cellulose acetate film support at a coverage of 459 mg of silver and 1040 mg of gelatin per square foot. No undesirably rapid setting of the emulsion occurs to interfere with coating as occurs, for example, with aldehyde hardeners. A sample of each film coating can then be examined for hardness after three days incubation at 38°C and 50 percent relative humidity by immersing in water at 20°C for 5 minutes and calculating the percentage swell of the emulsion. The incubation fog values are obtained from identical emulsion coatings after a two-week period of incubation at 40°C and 50 percent relative humidity. The coatings are exposed on an Eastman 1B sensitometer, processed for 5 minutes in a methyl-p-aminophenol-hydroquinone developer, fixed, washed and dried. The hardeners and hardened coatings pose no significant hazard to manufacturing personnel in terms of toxicity. Comparative data obtained in actual runs is set forth in Table I as follows:

TABLE I

| Hardener | Swell Control | Swell Hardener | | | Swell Relative to Control* | | | 2 Weeks, 50 percent Relative Humidity, 49°C Incubation Fog | | |
|---|---|---|---|---|---|---|---|---|---|---|
| | | 1 % | 3 % | 6 % | 1 % | 3 % | 6 % | Control | 1 % | 3 % |
| I | 590 | 490 | 320 | 290 | 83 | 54 | 49 | 0.79 | 0.37 | 0.15 |
| II | 710 | 370 | 310 | 270 | 52 | 44 | 38 | 0.43 | 0.14 | 0.12 |
| III | 590 | 380 | N.R. | 450 | 64 | N.R. | 76 | 0.79 | 0.73 | 0.61 |
| IV | 710 | 500 | 400 | 380 | 70 | 56 | 53.5 | 0.79 | 0.48 | 0.19 |
| V | 680 | 490 | 440 | N.R. | 72 | 65 | N.R. | 0.64 | 0.42 | 0.17 |
| VI | 810 | 390 | N.R. | N.R. | 48 | N.R. | N.R. | 1.07 | 0.60 | N.R. |
| VII | 720 | 490 | N.R. | N.R. | 68 | N.R. | N.R. | 1.07 | 0.44 | N.R. |
| VIII | 740 | 490 | 360 | N.R. | 66 | 49 | N.R. | 0.79 | 0.50 | 0.24 |
| IX | 800 | 390 | 330 | 280 | 49 | 41 | 35 | 0.80 | 0.27 | 0.30 |
| X | 720 | 330 | 240 | 210 | 46 | 33 | 29 | 0.75 | 0.28 | 0.10 |
| XI | 890 | 420 | 310 | 290 | 47 | 35 | 33 | 0.94 | 0.31 | 0.13 |
| XII | 750 | 430 | 390 | 330 | 57 | 52 | 44 | 1.10 | N.R. | 0.17 |

N.R. — No run undertaken
*Control = 100

Comparison with Known Toxic Hardener

Bis(2-chloroethyl) sulfone, a known toxic hardener, does not exhibit the degree of high temperature hardening nor the freedom from after-hardening that characterizes the hardeners of this invention. In a specific comparison bis(2-chloroethylsulfonyl)methane and bis(2-chloroethyl) sulfone are incorporated into separate portions of a magenta dye-forming coupler film emulsion in the manner described above in connection with Table I. Films coated with a single layer magenta coating containing 3 percent by weight bis(2-chloroethyl) sulfone based on the weight of dry gelatin (0.157 mol. hardener/g. gelatin) are not provided with sufficient high temperature hardening to permit color development processing at 86°C, while 3 percent by weight bis(2-chloroethylsulfonyl)methane, based on dry gelatin weight, allows successful color development processing of otherwise idential film coatings at temperatures of 125°C. This illustrates a dramatic improvement in high temperature hardening characteristics.

To compare after-hardening characteristics it is noted that the above film coatings hardened with 1 and 2 percent bis(2-chloroethylsulfonyl)methane decrease in percent swell (based on original coating thickness) only 14 and 16 percent, respectively, after incubation at 49°C and 50 percent relative humidity for 7 days. In direct comparison, with 3 percent by weight bis(2-chloroethyl) sulfone present in a similar film coating a change in swell of 103 percent is noted after incubation, indicating a much more pronounced after-hardening has occurred.

The invention has been described in detail with particular reference to preferred embodiments thereof but it will be understood that variations and modifications can be effected within the spirit and scope of the invention.

What is claimed is:

1. A compound having the structural formula:

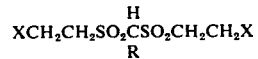

in which X is halogen and R is hydrogen, a phenyl or alkyl having from 1 to 6 carbon atoms.

2. A compound according to claim 1 in which the halogen is chlorine.
3. Bis(2-chloroethylsulfonyl) methane.
4. 1,1-Bis(2-chloroethylsulfonyl) ethane.
5. Alpha, alpha-Bis(2-chloroethylsulfonyl) toluene.

* * * * *